United States Patent [19]

Klemarczyk

[11] Patent Number: 4,806,608

[45] Date of Patent: Feb. 21, 1989

[54] CURABLE SILOXANE MALEIMIDE COMPOSITION

[75] Inventor: Philip Klemarczyk, Collinsville, Conn.

[73] Assignee: Loctite Corporation, Newington, Conn.

[21] Appl. No.: 26,535

[22] Filed: Mar. 16, 1987

[51] Int. Cl.⁴ .......................................... C08F 122/40
[52] U.S. Cl. .................................... 526/262; 526/248; 526/279
[58] Field of Search ................... 526/262, 279, 248

[56] References Cited

U.S. PATENT DOCUMENTS

| | | | |
|---|---|---|---|
| 3,325,450 | 6/1967 | Holub | 260/46.5 |
| 4,011,279 | 3/1977 | Berger et al. | 260/824 |
| 4,139,547 | 2/1979 | Berger | 260/448.2 |
| 4,338,426 | 7/1982 | Sato et al. | 528/26 |
| 4,364,808 | 12/1982 | Lohmann et al. | 204/158 |
| 4,395,527 | 7/1983 | Berger | 528/26 |
| 4,404,350 | 9/1983 | Ryang | 528/26 |
| 4,458,164 | 7/1984 | Lane | 307/519 |
| 4,472,565 | 9/1984 | Ryang | 528/26 |
| 4,535,099 | 8/1985 | Lee et al. | 521/154 |
| 4,565,873 | 1/1986 | Lohmann et al. | 548/110 |
| 4,581,461 | 4/1986 | Rossi et al. | 548/406 |
| 4,624,888 | 9/1987 | St. Clair et al. | |
| 4,656,235 | 4/1987 | Tesoro et al. | 526/262 |

OTHER PUBLICATIONS

Shubha Maudgal and Terry L. St. Clair, 29th National SAMPE Symposium, Apr. 3–5, 1984, p. 446.
Polyimidothioethers*, J. Poly. Sci. Polymer Chem. Ed. 14 159–182 (1976).

*Primary Examiner*—Harold D. Anderson
*Attorney, Agent, or Firm*—Vidas & Arrett

[57] ABSTRACT

Bis-maleimide compounds of the formula:

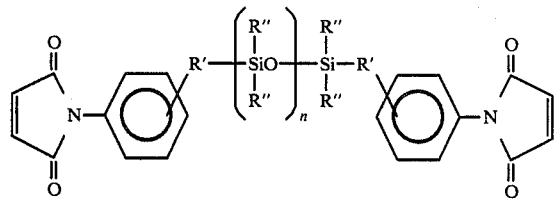

where R' is an alkenylene or alkylene group; the R" groups are independently hydrocarbon or halohydrocarbon groups; and n is an integer, are hydrolytically stable compounds which may be thermally cured, or co-cured with other radically cureable monomers, to provide crosslinked polymer with good thermal properties. Compounds of the formula where n is above about 9 can be used as additives for radically cureable silicone formulations.

8 Claims, No Drawings

CURABLE SILOXANE MALEIMIDE COMPOSITION

BACKGROUND OF THE INVENTION

Bis-maleimides are known to possess excellent thermal stability with no significant decomposition up to 350°–400°, however, when cured, they produce a very brittle polymer. In addition, they possess only limited solubility in common organic solvents. Silicone imide compounds of various types are known in the art. For example, from U.S. Pat. No. 4,364,808; 4,338,426; 4,139,547; 4,395,527; 4,011,279; 3,325,450; 4,472,565; 4,404,350; and 4,472,565. Silicone imide compounds have been disclosed as providing improved toughness and/or thermal properties over conventional silicones and as providing processing and curing advantages over ordinary polyimides.

U.S. Pat. No. 4,624,888 discloses ethynyl terminated polyimide siloxanes which are formed by reaction of controlled molar ratios of aminophenylacetylene aromatic dianhydrides and diaminosiloxanes.

In U.S. Pat. No. 4,581,461 there are described compounds of the formula:

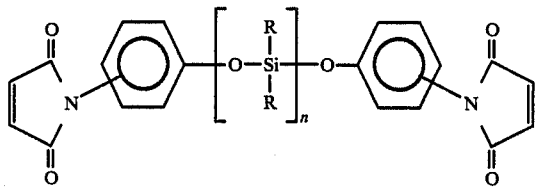

where n=1-6. These compounds are formed by reacting amino terminated dimethylsiloxanes of 1-6 repeat units. The compounds are said to be useful as crosslinking agents in adhesive systems. These compounds, however, contain Si—O—C bonds which are known to be hydrolytically unstable.

In U.S. Pat. No. 4,535,099 there are disclosed polyimide foams prepared by reaction of an organic tetracarboxylic acid ester with (a) a diamine of the formula:

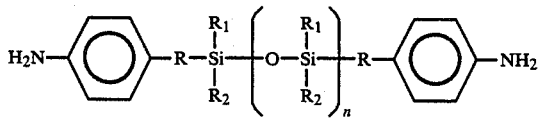

where R is a $C_2$ to $C_6$ alkylene group, $R_1$ and $R_2$ are each independently lower alkyl and n is an integer of 1-4, and (b) an aromatic diamine.

SUMMARY OF THE INVENTION

The present invention pertains to novel polysiloxane maleimide compounds which, like those of U.S. Pat. No. 4,581,461 can be used as additives in free radically curable adhesive sealant or coating formulations as crosslinkers and to improve the thermal properties of the cured formulations. Unlike the compounds of U.S. Pat. No. 4,458,164, however, the inventive compounds do not contain any of the hydrolytically unstable Si—O—C bonds.

The inventive maleimide compounds may be represented by the formula:

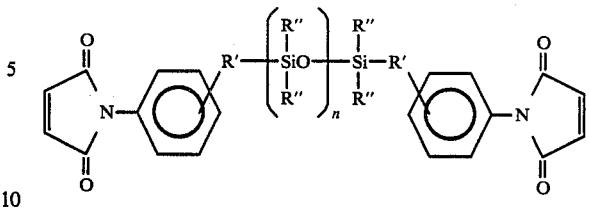

where R' is an alkenylene or alkylene group; the R" groups are independently selected from hydrocarbon and halohydrocarbon groups; and n is an interger of at least one. Suitable R' groups are —CH=CH— and —$C_3H_6$—. Suitable R" groups are methyl, ethyl, phenyl, and trifluoropropyl.

DETAILED DESCRIPTION OF THE INVENTION

The inventive maleimide compounds may be prepared by hydrosilation of aromatic maleimide compound of the formula:

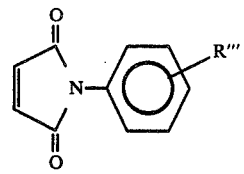

where R''' is an alkenyl or alkynyl group, with a SiH terminated polydiorganosiloxane (the organo groups being defined as for R"). The resulting silicone maleimide compounds, when thermally cured, give polymers having strengths comparable to commercially available maleimide compounds, at least up to MW about 750. The lowest molecular weight materials (n=1 to about 5) are waxy yellow solids while the remainder are viscous, yellow orange oils. The lowest molecular weight materials are compatible with organic monomers such as organic acrylic and methacrylic monomers whereas higher molecular weight materials, especially those where n is greater than about 9 are compatible with silicone formulations.

The compounds cure at about 200° C. and show no significant weight loss in thermal gravimetric analysis up to about 400°.

The inventive compounds may be thermally cured alone or in admixture at levels of between 1% and 95% with other radically cureable monomers such as acrylate and methacrylate esters. The (meth)acrylic esters may be selected from organic mono or poly (meth)acrylates and silicones having two or more pendant or terminal acrylate or methacrylate groups. The maleimide compounds of the invention may be thermally cured with or without added initiator. Radical initiators which are suitable include peroxide and azonitrile initiators.

The invention can be better illustrated by reference to the following non-limiting examples:

PREPARATIVE EXAMPLES

All reactions were performed under an inert atmosphere using dry reagents. The products of all reactions yielded spectral data consistent with the desired compound. Melting points are uncorrected.

Preparative Example 1

Preparation of 3-Ethynylphenyl Maleimide

A one liter flask equipped with a mechanical stirrer, condenser, thermometer, mantle, addition funnel, and nitrogen inlet was charged with 3-ethynyl aniline (125 g, 1.07 mole) and 250 ml of acetone. Maleic anhydride (104.5 g, 1.07 mole) was dissolved in 250 ml of acetone and this solution was added dropwise over 15 minutes. An exotherm to 31° C. occurred and a thick yellow precipitate formed. After stirring 30 minutes at ambient temperature, triethylamine (25 ml) and nickel (II) acetate (1.0 g, 8.5 mmole) were added and the mixture was heated to reflux. Acetic anhydride (120 g, 1.18 mole) was added dropwise over a 20 minute period. During the addition everything dissolved into a dark orange solution. After heating at reflux for three hours, 10 ml of water was added to quench excess acetic anhydride. The solution was cooled, and concentrated under reduced pressure. The residue was added to 1700 ml of water and the crude product precipitated as a yellow solid. It was filtered and washed consecutively with 500 ml of sat. aq. $Na_2CO_3$ and 1000 ml of water. The product was recrystallized from 1500 ml of ethanol filtered and vacuum dried at 60° C. for three hours at 0.5 mm/Hg. Yield=158.6g (75%) M.p.=129°–131° C.

Preparative Example 2

Preparation of 4-Vinylphenyl Maleimide

The above procedure was used to synthesize 4-vinyl phenyl maleimide with the following starting materials 4-aminostyrene (10.7 g, 90 mmol), maleic anhydride (8.8 g, 90 mmol), acetone (100 ml), triethylamine (2 ml), nickel (II) acetate (0.1 g, 0.85 mmol), acetic anhydride (114 g, 112 mmol), BHT (0.1 g). Yield=12.6g (70%). M.p.=124°–127° C. (with polymerization).

Preparative Example 3

Preparation of 4-Butenyloxy-1-Nitrobenzene

A 500 ml flask equipped with a mechanical stirrer, condenser, thermometer, and heating mantle was charged with p-nitrophenol (30.0 g, 216 mmol), 4-bromo-1-butene (29.1 g, 216 mmol), potassium carbonate (32.8 g, 237 mmol) and DMF (300 ml). The reaction mixture was heated to reflux and stirred for 48 hours. It was then cooled and solvent removed under reduced pressure. The residue was dissolved in 250 ml of methylene chloride and washed repeatedly with water to remove traces of DMF. The methylene chloride layer was dried ($M_gSO_4$), filtered, and solvent removed under reduced pressure. The product was used without further purification for the next step. Yield=7.0g (17%).

Preparative Example 4

Preparation of 4-Butenyloxyaniline

A 200 ml flask equipped with a mechanical stirrer, condenser, thermometer and heating mantle was charged with iron powder (26.0 g, 464 mmol) and 30 ml of water. This mixture was heated on a steam bath for 30 minutes. Concentrated hydrochloric acid (7 ml) and 4-butenyloxynitrobenzene (14.0 g, 72 mmol) were added dropwise simultaneously. After the addition was complete, the reaction mixture was stirred on a steam bath for an additional four hours. The reaction mixture was quenched by slowly adding a solution of sodium hydroxide (7.0 g, 175 mmol) in 15 ml of water and it was filtered hot. The filtrate was washed twice with 100 ml of hot benzene. The organic layers were combined, dried ($MgSO_4$), and filtered. Solvent was removed under reduced pressure and the product was vacuum dried for three hours at 50° C. and 0.8mm/Hg. Yield=4.0g (34%).

Preparative Example 5

Preparation of 4-Butenyloxyphenyl Maleimide

The procedure is the same for 3-ethynylphenyl maleimide. The following amounts of staring materials were used: 4-butenyloxyaniline (4.0 g, 24.5 mmol), maleic anhydride (2.4 g, 24.5 mmol), acetone (100 ml) triethylamine (5 ml), nickel (II) acetate (0.25 g, 3.5 mmol), and acetic anhydride (2.75 g, 27 mmol). Yield=5.0 g, (84%).

Preparative Example 6

Hydrosilation of 3-Ethynylphenyl Maleimide with a 400MW Si-H Terminated Polydimethyl Siloxane A 50 ml flask equipped with a magnetic stirrer, condenser, thermometer, heating mantle, and nitrogen inlet was charged with 3-ethynylphenyl maleimide (2.5 g, 12.9 mmol), 400MW Si-H terminated polydimethyl siloxane (5.0 g, 7.1 mmol), toluene (25 ml), and 2% chloroplatinic acid hexahydrate in butylacetate (0.2 g, 10 ppm Pt). The solution was heated to reflux, and after one hour, an IR sample revealed that the Si—H absorption had disappeared. The solution was cooled, filtered, and solvent removed under reduced pressure. The product was dried for one hour at 75° C. and 0.5 mm/Hg Yield=7.1 g (95%)

Preparative Example 7

Synthesis of a Series of Maleimide Terminated Silicones

The procedure of preparative Example 6 was employed for the synthesis of a number of maleimide terminated silicones. The table below provides the number of reactions, the silicone MW, silicone type, maleimide capping agent, and yield. The copolymer contains about 30% diphenyl siloxane units.

TABLE I

Silicone-Maleimide Polymers

| Silicone MW | Silicone type | Maleimide Capping Agent | Yield (%) |
|---|---|---|---|
| 134 | dimethylsiloxane | 3-Ethynylphenyl Maleimide | 88 |
| 400 | " | 3-Ethynylphenyl Maleimide | 94 |
| 750 | " | 3-Ethynylphenyl Maleimide | 95 |
| 1000 | " | 3-Ethynylphenyl Maleimide | 98 |
| 1600 | " | 3-Ethynylphenyl Maleimide | 98 |
| 1600 | dimethyl-diphenyl siloxane copolymer | 3-Ethynylphenyl Maleimide | 94 |
| 5000 | dimethyl siloxane | 3-Ethynylphenyl Maleimide | 95 |
| 400 | dimethyl siloxane | 4-butenyloxyphenyl Maleimide | 75 |

Preparative Example 8

Attempt to Hydrosilate 4-Vinylphenyl Maleimide

When preparation Example 6 was repeated using 4-vinylphenyl maleimide in place of 3-ethynylphenyl maleimide the maleimide homopolymerized instead of undergoing a hydrosilation reaction.

Preparative Example 9

Synthesis of 4-Hydroxyphenyl Maleimide 4-hydroxyphenyl maleimide was prepared by the same procedure as for 4-ethynylphenyl maleimide with the following starting materials aminophenol (54.5 g, 0.50 mole) maleic anhydride (49.0 g, 0.50 mole), acetone (500 ml), triethylamine (11 ml), nickel (II) acetate (0.5 g, 43 mmol), and acetic anhydride (63.8 g, 0.625 mol).

Preparative Example 10

Reaction of 4-Hydroxyphenyl Maleimide with Bis-dimethylaminooctamethyl-tetrasiloxane (BDOT)

A 50 ml flask equipped with a magnetic stirrer, condenser, thermometer, heating mantle, and nitrogen inlet was charged with BDOT (4.3 g, 12 mmol), 4-hydroxyphenyl maleimide (4.5 g, 24 mmol), and chlorobenzene (25 ml) and the solution was heated to reflux. After heating at reflux overnight, methanol (1 ml) was added to quench any Si—N(CH3)2, remaining. Solvent was removed under reduced pressure and the product was vacuum dried for two hours at 60° and 0.5 mm/Hg Yield=8.1 g (100%).

Hydrolytic Stability

One gram each of (a) the inventive maleimide silicone from preparative Example 6, and (b) the maleimide silicone of U.S. Pat. No. 4,581,461 from preparation Example 10 were placed in separate vials and two drops of water added. After 36 hours the samples were dried and analyzed by GPC. The Example 6 product showed no change between the GPC of the water treated sample and an untreated sample. The Example 10 product showed a significant difference in the retention times of the product after water treatment compared to the retention time of the untreated product.

Cure Testing

The maleimide terminated silicone products of Preparative Example 7 were placed between mild steel lapshear coupons and cured overnight at 232° C. An organic bis-maleimide control (Mitsui-Toatsu M-20) was also cured in the same manner. The tensile shear strengths were then measured. The results, given in Table II below show that the strengths of the inventive materials are comparable to the organic controls up to silicone MW about 750 (i.e., n=about 9). Moreover, even the 5000 MW dimethyl Silicone product of the invention gave a stronger tensile shear value than the 400 MW silicone capped with 4-butenoxyphenyl maleimide.

TABLE II

| Tensile Shear Strengths of Maleimide Silicones | | | |
|---|---|---|---|
| Silicone MW | Maleimide Capping Agent | Silicone Type | Tensile Shear Strength (psi) |
| — | Mitsui-Toatsu M-20 | — | 1024 |
| 134 | 3-Ethynylphenyl Maleimide | Dimethyl | 1010 |
| 400 | 3-Ethynylphenyl Maleimide | Dimethyl | 1250 |
| 750 | 3-Ethynylphenyl Maleimide | Dimethyl | 903 |
| 1000 | 3-Ethynylphenyl Maleimide | Dimethyl | 656 |
| 1600 | 3-Ethynylphenyl Maleimide | Dimethyl | 155 |
| 5000 | 3-Ethynylphenyl Maleimide | Dimethyl | 122 |
| 1600 | 3-Ethynylphenyl Maleimide | Diphenyl-Dimethyl | 335 |
| 400 | 4-Butenoxyphenyl Maleimide | Dimethyl | 45 |

What is claimed is:

1. a free radically curable adhesive or sealant formulation comprising between 1% and 95% of a compound of the formula:

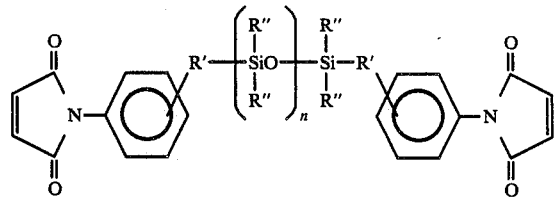

where R' is an alkylene or alkenylene group; the R" groups are independently selected from hydrocarbon or halohydrocarbon groups; and n is an interger of at least one; and between 5% and 99% of a second free radically curable compound.

2. A composition as in claim 1 where R' is alkenylene.

3. The composition of claim 2 where R' is ethenylene and R" is selected from the group consisting of methyl, ethyl, phenyl, and trifluoropropyl.

4. The composition of claim 1 where n is 1–9.

5. The composition of claim 1 where n is greater than about 9.

6. A composition as in claim 1 wherein said second free radically cureable compound is selected from the group consisting of (meth)acrylic esters.

7. A composition as in claim 6 wherein said second free radically curable compound is a silicone having two or more pendant or terminal acrylate or methacrylate groups.

8. A crosslinked imide polymer prepared by thermally curing a compound of the formula:

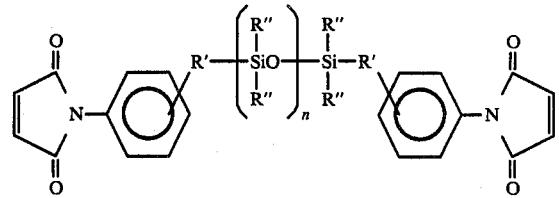

where R' is an alkylene or alkenylene group; the R" groups are independently selected from hydrocarbon or halohydrocarbon groups; and n is an integer of at least one.